United States Patent [19]

Thrasher

[11] Patent Number: 4,914,041

[45] Date of Patent: Apr. 3, 1990

[54] REAGENT AND METHOD FOR DETECTING RHEUMATOID FACTOR

[75] Inventor: Caron C. Thrasher, Diamond Bar, Calif.

[73] Assignee: Beckman Instruments, Inc., Fullerton, Calif.

[21] Appl. No.: 155,661

[22] Filed: Feb. 12, 1988

[51] Int. Cl.$^4$ .......................................... G01N 33/564
[52] U.S. Cl. .................................... 436/509; 436/821; 436/825
[58] Field of Search ....................... 436/509, 821, 825; 536/21; 514/56

[56] References Cited

U.S. PATENT DOCUMENTS

| | | | |
|---|---|---|---|
| 3,634,123 | 1/1972 | Eriksson | 514/56 |
| 4,153,417 | 5/1979 | Hallgren et al. | 23/230 |
| 4,184,847 | 1/1980 | Hällgren | |
| 4,282,002 | 8/1981 | Prodell | 23/230 |
| 4,397,960 | 8/1983 | Moussebois et al. | 436/512 |
| 4,451,458 | 5/1984 | Bühlmann | 514/56 |
| 4,640,897 | 2/1987 | Leynadier | 436/501 |

FOREIGN PATENT DOCUMENTS 3615384 11/1986 Fed. Rep. of Germany ...... 436/509

OTHER PUBLICATIONS

D. R. Burton et al., "The C1q Receptor Site on Immunoglobulin G"; *Nature*, 288, 338–344, (1980).

Emanuel et al., "Formation of Complement Subcomponent C1q-Immunoglobulin G Complex", *Biochem. J.*, 205, 361–372, (1982).

Desjarlais et al., "Rheumatoid Factors Measured in Serum with a Fully Automated Laser Nephelometer and Correlation with Agglutination Tube Titers", *Clin. Chem.*, 31(6), 1077–1078, (1985).

Jones et al., "Quantitation of Rheumatoid Factor Activity by Nephelometry", *Am. J. Clin. Path.*, 72(3), 432–436, (1979).

Painter et al., "Performance of a New Rate-Nephelometric Assay for Rheumatoid Factor and its Correlation with Tube-Titer Results for Human Sera and Synovial Fluid", *Clin. Chem.*, 28(11), 2214–2218, (1982).

Borque et al., "Turbidimetry of Rheumatoid Factor in Serum with a Centrifuge Analyzer", *Clin. Chem.*, 32(1), 124–129, (1986).

Finley et al., "Rate Nephelometric Measurement of Rheumatoid Factor in Serum", *Clin. Chem.*, 25(11), 1909–1914, (1979).

Nakamura et al., "New Developments in Light Scattering Immunoassay Methods", *Clinical Laboratory Assays*, Chapter 1, 1–15, (1983).

Cohen, *Rheumatology and Immunology*, 77–80.

McDuffie, *Laboratory Diagnostic Procedures in the Rheumatic Diseases*, Chapter 4, 95–124, (1985).

*Primary Examiner*—Robert J. Hill, Jr.
*Attorney, Agent, or Firm*—William H. May; Arnold Grant

[57] ABSTRACT

A reagent for use in immunoassays for rheumatoid factor (RF) is provided. The reagent contains heparin. Use of this reagent suppresses interference from the component C1q found in some test samples, and alleviates the need for a heat inactivation pretreatment of test samples to eliminate C1q interference.

20 Claims, 3 Drawing Sheets

REAGENT AND METHOD FOR DETECTING RHEUMATOID FACTOR

BACKGROUND OF THE INVENTION

Rheumatoid arthritis is a systemic disease characterized by muscular pain and stiffness as well as articular inflammation and destruction. These symptoms are primarily the result of antibodies, sometimes referred to as autoantibodies, which react with an individual's own immunoglobulin antibodies. The precise cause of rheumatoid arthritis is unknown, but there is evidence that three different factors are involved, namely: (1) genetic predisposition to rheumatoid arthritis; (2) environmental factors, such as viral infection; and, (3) a functional defect in T-lymphocytes. The interrelationship among the genetic, environmental, and immunologic factors is not known.

Evidence of altered immune functions which bring about symptoms of rheumatoid arthritis include hypergammaglobulinemia, decreased in vivo and in vitro T-lymphocyte reactivity, and the presence of autoantibodies to immunoglobulin G (IgG). These "antiantibodies" or "antiimmunoglobulins" have been named rheumatoid factors (RF) because of their association with rheumatoid arthritis. RF has also been found with varying frequency in patients with most of the connective tissue diseases, many chronic and sub-acute infections, and a variety of miscellaneous disorders. In addition, RF has been found in many apparently healthy persons, particularly the elderly.

In spite of its lack of specificity for the diagnosis of rheumatoid arthritis, RF is still of value as a prognostic indicator. For example, studies have shown that high quantities or titers of RF are associated with destructive joint disease, the presence of rheumatoid nodules, and the likelihood of developing numerous systemic complications. Changes in the titer of RF during the course of the illness are not very helpful in assessing the course of the disease in a given individual. Nonetheless, in studies of groups of patients treated with pharmacologic agents, mean titers of RF generally decline if improvement occurs. Over one-half of patients with seropositive rheumatoid arthritis who go into remission become seronegative. However, about 25% of such individuals continue to have high titers in their sera in spite of clinical recovery.

The multivalent RF autoantibody specifically binds to the monovalent Fc portion, or tail, of the IgG class of immunoglobulin antibodies. RF is thus capable of binding to the IgG antibody while one or more of the binding arms of the IgG antibody is/are bound to its corresponding antigen. In fact, it is believed that RF is more attracted to the IgG antibody in its bound form due to conformational changes that take place in the IgG antibody, rendering the Fc portion of the antibody more accessible.

The most commonly used test for RF is the latex agglutination method of Singer and Plotz, sometimes referred to as the latex fixation test. Singer, J. M., and Plotz, C. M., "The latex fixation test. I. Application to the serologic diagnosis of rheumatoid arthritis", Am. J. Med., 21; 888-892 (1956). In this test, latex particles coated with human IgG are agglutinated on a slide, usually at a 1:20 dilution of test sample. The test sample is typically human serum, although Synovial fluid (taken from a suspected arthritic joint), is also analyzed on occasion. This test is generally regarded as a screening procedure from which a yes/no result can be obtained. A gross estimate of titer can be achieved by further serial dilutions of the serum utilizing the original latex tube test. In the latex tube test, the latex particle is agglutinated in solution, with the resulting agglutination being visually interpreted according to various standards and controls. The tube dilution test has the advantage of being considerably more sensitive than the slide test, but it is more cumbersome to perform.

The latex agglutination test, which is performd visually rather than instrumentally (such as with nephelometry), is the principle behind most of the subsequently devised methods for detecting RF. These methods all involve use of an indicator system such as latex, bentonite, or erythrocytes, to which human IgG is attached. The presence of RF is recognized agglutination, flocculation, or precipitation of the various indicator systems.

Heat-aggregated IgG may also be used directly as the antigen or indicator system in the assay. The heat aggregation step is believed by some to impart a conformational change to the IgG resulting in better detection. The conformational change is believed to simulate the conformational change encountered when the IgG is bound to its corresponding antigen through one or more of its binding arms.

An earlier test known as the sensitized sheep cell agglutination test (Waaler-Rose test) is still employed in some clinical laboratories. Sheep cells coated with rabbit antibody to these erythrocytes are agglutinated by certain RF. However, it is important first to remove any anti-sheep cell antibodies from the test sample by suitable absorption so as not to produce false-positive test reactions. Moreover, one must use fresh sheep cells that are standardized each day before use. This necessity for fresh cells makes the assay somewhat awkward to perform on a routine basis, although some believe the sheep cell agglutination test may have more specificity for the RF of rheumatoid arthritis.

Other available tests are a more direct variation of the original latex agglutination test. For example, a flocculation test using bentonite particles, rather than latex, coated with aggregated human IgG as the indicator system is used in some laboratories. Formalinized and "tanned" sheep cells; i.e., cells which have been preserved, can be coated with aggregated human IgG as the indicator system. These cells are then agglutinated by RF. This test is very sensitive, but the assay is somewhat more difficult to perform than the latex tests and may not lead to any practical advantage in routine studies. A radioimmunoassay for IgM RF has also been developed wherein insolubilized IgG is used as an immunoabsorbent from which RF can be eluted and characterized. Immunodiffusion tests have likewise been developed, employing both double and single diffusion methodologies.

Automated nephelometric or turbidimetric procedures can generally be employed using any variety of indicator systems. In turbidimetry, the reduction of light transmitted through the suspension of particles, or aggregates, is measured. The reduction is caused by reflection, scatter, and absorption of the light by the aggregates. In nephelometry, it is the light scattered or reflected toward a detector that is not in the direct path of light which is measured. Where automation is unavailable or impractical, a simpler version of nephelometry and turbidimetry is available wherein the amount of aggregation observed in a test sample is visually compared to a single standard or a series of standard controls.

In addition to the aforementioned indicator systems, heat aggregated IgG can be used directly as the indicator system. The primary drawback to the use of heat aggregated IgG as the indicator system is the uncontrolled, random orientation of the Fc portion of the IgG that is obtained in the heat aggregation process. Where latex, bentonite, or similar particles are used at the core of the indicator system, either intact IgG antibodies or Fc fragments can be used, with the number and orientation of Fc binding sites more easily controlled, depending upon the particular method of attachment employed. Regardless of the type of indicator system selected, nephelometric and turbidimetric methods provide a major advantage in that they are an objective analysis by an instrument of what has traditionally been a visual, highly subjective assessment of particle agglutination expressed in titration steps.

Serum or synovial fluid to be tested for RF must ordinarily be heated at 56° C. before assay to inactivate the labile complement component Clq. The Clq component, frequently present in serum samples, has been described as a multivalent "bunch of tulips" wherein each "tulip" is capable of binding to the same Fc portion of the IgG antibody as RF. Consequently, any Clq present in a test sample is also capable of agglutinating particles coated with IgG, thus resulting in false-positive reactions.

The entire heat inactivation step consumes approximately 45 minutes. Each sample must first be subjected to incubation at 56° C.±1° C. for 30 minutes ±1 minute. The samples are then microcentrifuged for 5 minutes. Further sample handling uses the remaining approximately 10 minutes. This required pretreatment of samples imposes an additional time-consuming procedure in RF assay that must generally be incorporated into every test.

In some instances the pretreatment, or heat inactivation step, has been avoided where the latex slide agglutination and/or latex tube tests have been employed. Avoidance of the heat inactivation step in these tests has generally required the use of a standard glycine buffer and large dilutions of Clq. For example, serial dilutions of 1:20 through 1:10240 are used in the standard latex tube test. The glycine compound is believed to have some inhibitory effect on Clq.

Each RF assay, however, has different requirements with regard to characteristics such as assay precision. Most nephelometric and turbidimetric assays, for example, provide objective numerical data, as opposed to visual interpretation within a given concentration range. These automated types of nephelometric and turbidimetric assays are unable to tolerate the heavy dilutions of serum sample required in the visual latex agglutination and latex tube tests to sufficiently dilute out the interfering Clq from a test sample. Adjustment of this parameter is therefore unavailable in typical nephelometric and turbidimetric RF assays.

Use of a glycine buffer alone has proved to be ineffective in universal application to automated nephelometric and turbidimetric RF assays. Other known Clq inhibitors, such as diaminobutane or deoxyribonucleic acid (DNA) disclosed in U.S. Pat. No. 4,153,417, have likewise proved to be unsatisfactory in these types of nephelometric and turbidimetric assays. These compounds are either ineffective in inhibiting Clq activity or concurrently inhibit RF activity to the detriment of the assay.

Because of the expense of the latex tube test, in terms of glassware, reagents, and technician time, and because of the deficiencies of the slide agglutination test, automated nephelometric and turbidimetric tests have become highly desirable. It would be advantageous to provide such a test without the requirement of a separate pretreatment step of inactivate Clq.

SUMMARY OF THE INVENTION

A reagent for use in the detection of RF in serum and synovial fluid samples is provided in accordance with the present invention. The reagent contains IgG antibodies with Fc portions thereof exposed, a buffer, and heparin. It has surprisingly been found that heparin acts as an inhibitor of the interferent Clq without significantly inhibiting the activity of RF, thus eliminating the need for the cumbersome and time consuming heat inactivation pretreatment step required in prior art procedures. The reagent of the present invention is particularly useful in nephelometric and turbidimetric assays and has surprisingly been found to impart greater temperature stability and improved precision to the assay of RF.

DETAILED DESCRIPTION OF THE INVENTION

Figure 1:
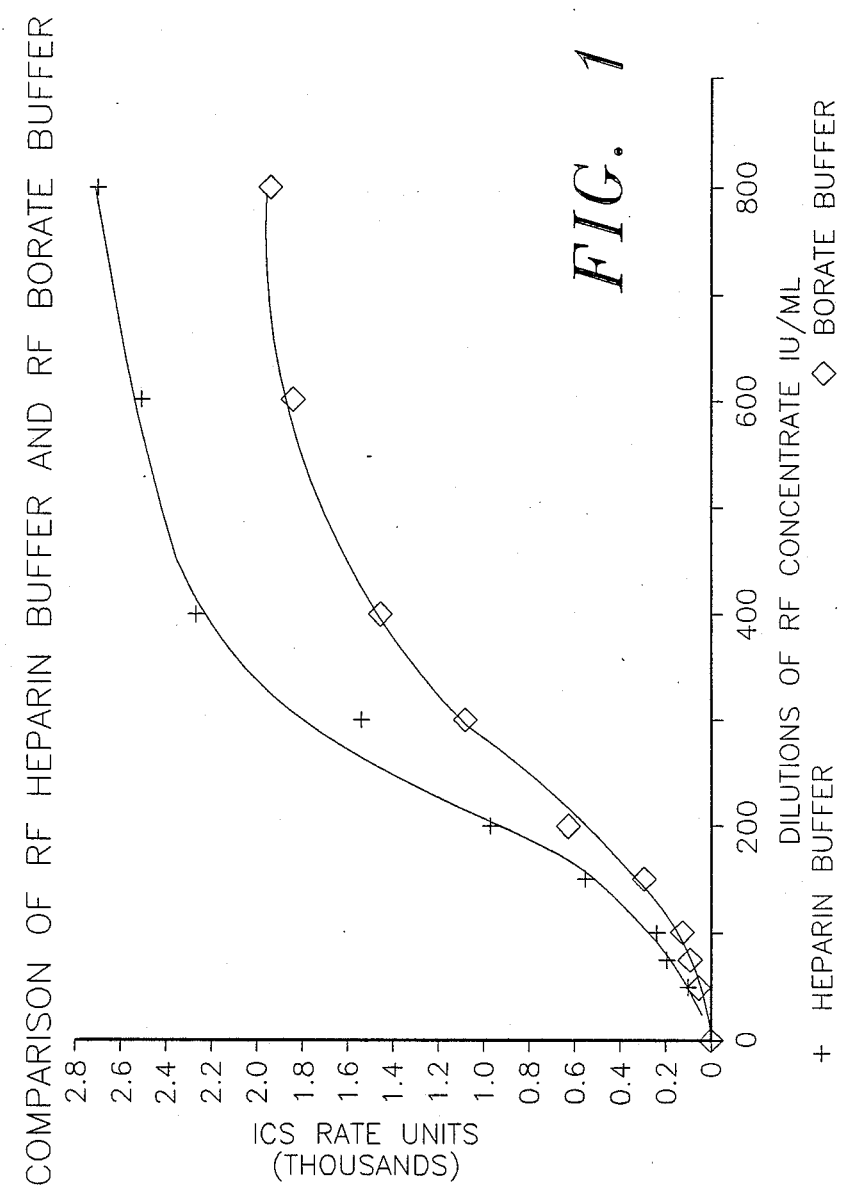
FIG. 1 is a graphic comparison of data from a nephelometric RF assay using the heparin reagent of the present invention without heat inactivation and the same assay using the prior art borate buffer reagent with heat inactivation.

Heparin is a mucopolysaccharide sulphuric acid ester that prolongs the clotting time of blood. Sodium heparin, as it is commercially available, is a mixture of active constituents having the property of prolonging the clotting time of blood. Sodium heparin is usually obtained from the lungs, intestinal mucosa, or other suitable tissues of cattle, sheep, hogs and other domesticated mammals used for food by man.

The activity of heparin is traditionally measured in the U.S. on the basis of U.S. Pharmacopeia (USP) units, which are to be distinguished from International Units (IU). The potency of sodium heparin, calculated on a dried basis, is usually not less than 120 USP Heparin Units in each mg when derived from lungs and usually not less than 140 USP Heparin Units in each mg when derived from other tissues, and typically not less than 90.0 percent and not more than 110.0 percent of the potency stated on the label.

In accordance with the present invention, at least about 750,000 USP Units of sodium heparin are added per liter of reagent solution to suppress Clq in an RF assay. Optimally, at least about 1,000,000 USP units per liter are added where the preferred phosphate buffer containing reagent of the present invention is employed.

Sodium heparin may be effectively added to any buffer capable of being used in an assay for RF. The optimal amount of heparin will, however, vary in accordance with the particular buffer selected. For example, a lower optimal amount of sodium heparin will generally be used in a glycine buffer, due to the fact that glycine reportedly has some inherent inhibitory effect on C1q. The upper limit of the amount of sodium heparin added to a particular buffer is generally dictated by economic considerations.

Buffers which are of use in an RF assay are generally those buffers having a buffering capacity in the pH range of about 7.0 to about 8.5. Traditional buffers of this type include phosphate, glycine, borate, and TRIS (tri-[hydroxymethyl]aminomethane), and derivatives thereof, such as glycylglycine. Also of use are certain of the newer biological buffers, including MOPS (3-[N-morpholino]propane sulfonic acid), TES (N-tris-[hydroxymethyl]methyl-2-amino ethane sulfonic acid), HEPES (N-2-hydroxyethylpiperazine-N'-2-ethane sulfonic acid), DIPSO (3-[N-bis-(hydroxyethyl)-amino]-2-hydroxy-propane sulfonic acid), TAPSO (3-[N-(trishydroxymethyl)methylamino]-2-hydroxypropane sulfonic acid), POPSO (piperazine-N,N'-bis-[2-hydroxypropane sulfonic acid]), HEPPSO (N-hydroxyethylpiperazine-N'-2-hydroxypropane sulfonic acid), TRICINE (N-tris[hydroxymethyl]methyl glycine) BICINE (N,N-bis-[2-hydroxyethyl]glycine), and TAPS (N-tris-[hydroxymethyl]methyl-3-aminopropane sulfonic acid). Mixtures of such buffers may also be used.

The formation of scattering centers, or agglomeration, can be accelerated by the use of hydrophilic nonionic polymers, such as dextran or polyethylene glycol (PEG), which increase the probability of protein-protein interaction by excluding a significant fraction of water. The use of polymers in a nephelometric assay also gives the advantages of increased sensitivity and less antiserum consumption.

Heparin has surprisingly been found to be an ideal C1q inhibitor for use in RF assay buffers, because of its greater specificity for C1q than some of the suggested prior art compounds such as diaminobutane and DNA. Specifically, heparin has been found to have much less of an inhibitory effect on RF where concentrations adequate to effect C1q inhibition are used. Moreover, the phosphate buffer with heparin added exhibited the same curve fit as the prior art borate buffer where heat inactivation pretreatment was employed, indicating an excellent correlation with the prior art method.

EXAMPLE 1

Formulation of Heparin Buffer

Two hundred liters of an RF buffer containing heparin were made up as follows:

TABLE I

| | CONSTITUENT | AMOUNT/L | QUANTITY USED |
|---|---|---|---|
| 1. | Sodium Heparin (Porcine Intestinal) | 1,000,000 USP Units | 200,000,000 USP Units |
| 2. | Potassium Phosphate Monobasic ($KH_2PO_4$) | 1.36 g | 272 g |
| 3. | Potassium Phosphate Dibasic ($K_2HPO_4$) | 1.74 g | 348 g |
| 4. | Sodium Chloride | 4.38 g | 876 g |
| 5. | Sodium Azide | 1.0 g | 200 g |
| 6. | Polyethylene Glycol (PEG) | 7.52 g | 1.496 kg |
| 7. | Ethylenediamine tetracetic acid (EDTA) | 6.36 mg | 1.265 g |
| 8. | Deionized water | 1.0 L | 200 L |

The constituents were dissolved in an excess of deionized water using a magnetic stirrer, and the resulting solution then brought up to volume using further quantities of deionized water. The heparin did not dissolve readily, and a mixing time of 30 minutes was required to fully effect dissolution.

EXAMPLE 2

A typical nephelometric immunoassay for RF was run using dilutions of a RF standard, heat aggregated IgG, and the heparin buffer from Example 1. These results were compared with the same assay using the prior art borate buffer in conjunction with a separate heat inactivation step.

RF concentrate was obtained from Aalto Scientific, Ltd., San Marcos, Calif. and used as an internal standard. The concentrate was diluted to the concentrations indicated in column 1 of Table II. Nephelometric measurements were taken on an ICS ™ nephelometer (Beckman Instruments) by placing 500 μL of heparin buffer into an ICS ™ vial (Beckman Instruments), and injecting 100 μL of neat sample from each RF standard dilution. An instrument gain setting of manual Mode M33 was used. After the injection transient subsided and the baseline was obtained, 42 μL of heat aggregated IgG (RF antigen ™, Beckman Instruments) was added and the instrument triggered to record the peak rate signal. The results are set forth in column 2 of Table II.

The diluted samples of RF standard were then heat inactivated for 30 minutes (±1 minute) at 56° C. (±1° C.), and subsequently centrifuged at 11,000 rpm for 5 minutes. Nephelometric measurements were again taken in the manner previously described with the exception that the prior art borate buffer was substituted for the heparin buffer.

TABLE II

| RF Standard (IU/mL) | Heparin Buffer | Borate Buffer |
|---|---|---|
| 0 | — | 10.8 |
| 51.7 | 55.0 | 30.9 |
| 77.6 | 95.0 | 58.0 |
| 103 | 240.0 | 112.5 |
| 155 | 545.0 | 286.0 |
| 207 | 952.5 | 619.7 |
| 310 | 1535.0 | 1060.0 |
| 414 | 2260.0 | 1443.3 |
| 621 | 2540.0 | 1850.0 |
| 827.5 | 2700.0 | 1946.7 |

The results, shown in Table II, are graphically depicted in FIG. 1, wherein it can be seen that the heparin buffer of the present invention yields data having the same curve fit as the data from the prior art heat inactivation method using standard borate buffer.

EXAMPLE 3

Temperature Sensitivity

The nephelometric RF assays from Example 2 were repeated at three different temperatures, namely 18° C., 25° C., and 32° C. using the same internal standard. The raw data from these assays were normalized against a target value established by referencing the internal standard to an outside control system such as that established by the College of American Pathologists, Reference Preparation for RF (CAP RPRF) or by the Center for Disease Control (CDC). The CAP RPRF Control System is traceable to the World Health Organization (WHO). CAP RPRF activity units are standardized to a scale that runs from about 20 to about 125 units. CDC activity units are reported as International Units (IU) and are standardized to a scale that runs from about 60 to about 400 IU.

The standards used for the nephelometric RF immunoassay using the heparin buffer of the present invention were standardized to CAP RPRF Units. A target rate value of 2084 was set for the concentration of 85.3 units/mL on the Beckman ICS ™ nephelometer, referencing to CAP RPRF Units. The results of these temperature sensitivity studies are shown in Table III. The same results are graphically depicted in FIG. 2.

TABLE III

| [Target] Units/mL | Heparin Buffer | | | | | | | |
|---|---|---|---|---|---|---|---|---|
| | 18° C. | | 25° C. | | | 32° C. | | |
| | Raw | Norm | Raw | Norm | % Diff from 18° C. | Raw | Norm | % Diff from 18° C. |
| 17.2 | 80 | 91 | 107 | 121 | 33.8 | 112 | 127 | 40.0 |
| 30.6 | 314 | 356 | 364 | 412 | 15.9 | 395 | 447 | 25.8 |
| 35.5 | 420 | 476 | 468 | 530 | 11.4 | 509 | 576 | 21.2 |
| 47.0 | 686 | 777 | 839 | 950 | 22.3 | 947 | 1073 | 38.0 |
| 70.8 | 1407 | 1594 | 1767 | 2001 | 25.6 | 1910 | 2163 | 35.7 |
| 85.3 | 1840 | 2084 | 2320 | 2628 | 26.1 | 2467 | 2794 | 34.1 |
| 106.0 | 2503 | 2835 | 2870 | 3251 | 14.7 | 3143 | 3560 | 25.6 |
| 141.0 | 3387 | 3836 | 3917 | 4436 | 15.6 | 4363 | 4942 | 28.8 |

The same internal RF standards were used for the nephelometric RF immunoassay using heat inactivation and the prior art borate buffer, but were standardized to CDC International Units. In all other respects, the procedure was the same as for the heparin buffer, except as noted in Example 2. A target rate value of 1470 was set for the concentration of 223.0 IU/mL on the Beckman ICS ™ nephelometer, referencing to the CDC system. The results of temperature sensitivity studies on the prior art procedure are shown in Table IV, and are graphically depicted in FIG. 3.

TABLE IV

| [Target] IU/ml | Borate Buffer/Heat Inactivation | | | | | | | |
|---|---|---|---|---|---|---|---|---|
| | 18° C. | | 25° C. | | | 32° C. | | |
| | Raw | Norm | Raw | Norm | From 18° C. | Raw | Norm | From 18° C. |
| 45.0 | 109 | 167 | 131 | 201 | 20.2 | 146 | 224 | 33.9 |
| 80.0 | 171 | 263 | 284 | 436 | 66.1 | 320 | 492 | 87.1 |
| 92.5 | 205 | 315 | 337 | 518 | 64.4 | 459 | 705 | 123.9 |
| 123.0 | 379 | 582 | 612 | 940 | 61.5 | 698 | 1072 | 84.2 |
| 185.0 | 775 | 1190 | 1243 | 1909 | 60.4 | 1483 | 2278 | 91.4 |
| 223.0 | 957 | 1470 | 1480 | 2273 | 54.6 | 1993 | 3061 | 108.3 |
| 270.0 | 1423 | 2186 | 2180 | 3349 | 53.2 | 2440 | 3748 | 71.5 |
| 330.0 | 1760 | 2704 | 2546 | 3911 | 44.7 | 3093 | 4751 | 75.7 |
| 370.0 | 1980 | 3041 | 2890 | 4439 | 46.0 | 3557 | 5464 | 79.6 |
| 444.0 | 2363 | 3630 | 3320 | 5100 | 40.5 | 3987 | 6124 | 68.7 |
| 500.0 | 2430 | 3733 | 3457 | 5310 | 42.3 | 4353 | 6687 | 79.1 |

Figure 2:
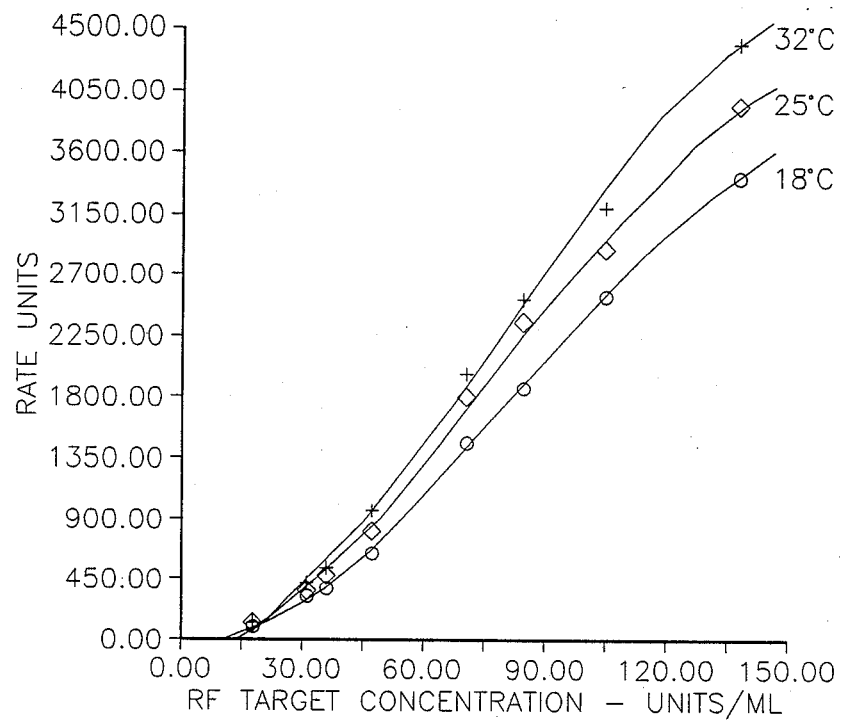
FIG. 2 graphically depicts the temperature stability of a nephelometric RF assay using the heparin reagent of the present invention.
Figure 3:
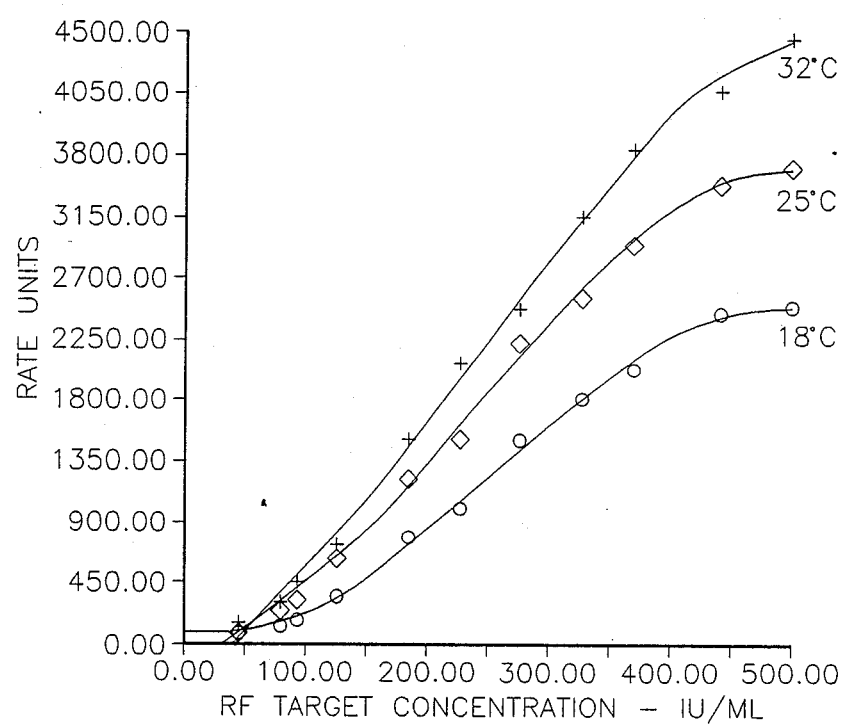
FIG. 3 graphically depicts the temperature stability of a nephelometric RF assay using the prior art borate buffer reagent.

A comparison of the graphs shown in FIG. 2 and FIG. 3 demonstrates the surprising resistance to temperature sensitivity of the heparin buffer of the present invention. Specifically, the nephelometric RF assay using the heparin buffer of the present invention exhibited an approximate 29% increase in rate units from 18° C. to 32° C., while an approximate 75% increase was observed where the prior art method was used employing the borate buffer and heat inactivation.

EXAMPLE 4

Precision

An aliquot of RF standard was diluted down to low level range, and nephelometric RF assay readings repeated twenty times each for the heparin buffer and for the borate buffer with heat inactivation. The measurements were taken from the same sample at 18° C. and at 25° C. as previously described in Examples 2 and 3. The ICS ™ nephelometer (Beckman Instruments) was programmed to report heparin buffer results in CAP RPRF Units and borate buffer results in CDC International Units. The results are set forth in Table V.

TABLE V

| | Low Level Precision | | | | | |
|---|---|---|---|---|---|---|
| | Heparin Buffer | | | Borate Buffer | | |
| Temp. | Mean | Standard Deviation | % Coeff of Var | Mean | Standard Deviation | % Coeff of Var |
| 18° C. | 39.10 | 1.49 | 3.81 | 100.40 | 9.43 | 9.40 |
| 25° C. | 36.30 | 0.46 | 1.26 | 100.10 | 4.27 | 4.27 |

An aliquot of the same RF standard was subsequently diluted down to a moderate range, considered to be RF positive. A repetition of 6 measurements were taken for the same sample using both the heparin buffer and the prior art heat inactivation method with standard borate buffer, at 18° C., 25° C., and 32° C. The results for the heparin buffer samples were reported in CAP RPRF Units, with the borate buffer results being reported in CDC International Units. The comparative data appears in Table VI.

TABLE VI

| | RF Positive Precision | | | | | |
|---|---|---|---|---|---|---|
| | Heparin Buffer | | | Borate Buffer | | |
| Temp. | Mean | Standard Deviation | % Coeff of Var | Mean | Standard Deviation | % Coeff of Var |
| 18° C. | 49.8 | 0.57 | 1.14 | 134.0 | 2.83 | 2.11 |
| 25° C. | 47.9 | 1.20 | 2.51 | 144.0 | 3.60 | 2.50 |

TABLE VI-continued

| | RF Positive Precision | | | | | |
|---|---|---|---|---|---|---|
| | Heparin Buffer | | | Borate Buffer | | |
| Temp. | Mean | Standard Deviation | % Coeff of Var | Mean | Standard Deviation | % Coeff of Var |
| 32° C. | 50.0 | 0.29 | 0.57 | 143.0 | 1.00 | 0.70 |

In most cases, the heparin buffer samples exhibited a significantly lower coefficient of variation. The data establishes the unusual finding of improved precision obtained from using the heparin buffer of the present invention.

As this invention may be embodied in several forms without departing from the essential spirit thereof, the invention is intended to be defined by the appended claims as opposed to the foregoing description.

I claim:

1. A reagent for use in an immunoassay for rheumatoid factor comprising a plurality of IgG antibodies with Fc portions thereof exposed, a buffer and an amount of heparin effective to inhibit any interference of Clq during use in the immunoassay.

2. The reagent of claim 1 wherein said heparin is present in a concentration of at least about 750,000 USP Units/L.

3. The reagent of claim 1 wherein said buffer has a buffering capacity in the pH range of about 7.0 to about 8.5.

4. The reagent of claim 3 wherein said heparin is present in a concentration of at least about 750,000 USP Units/L.

5. The reagent of claim 3 wherein said buffer is selected from the group consisting of phosphate, glycine, borate, TRIS, MOPS, TES, HEPES, DIPSO, TAPSO, POPSO, HEPPSO, TRICINE, BICINE, TAPS, and mixtures thereof.

6. The reagent of claim 5 wherein said heparin is present in a concentration of about 1,000,000 USP Units/L.

7. The reagent of claim 6 wherein said buffer is a phosphate buffer.

8. The reagent of claim 7 further comprising an amount of an hydrophilic nonionic polymer effective to promote agglomeration.

9. The reagent of claim 8 wherein the hydrophilic nonionic polymer is polyethylene glycol present in a concentration of at least about 7.5 g/L.

10. A method of measuring RF in a test sample comprising:
   a. contacting said test sample with an indicator system comprising a plurality of exposed Fc portions of IgG antibodies in the presence of heparin; and,
   b. detecting the presence of agglutination.

11. The method of claim 10 wherein said detection is performed instrumentally.

12. The method of claim 11 wherein said detection is performed by nephelometry or turbidimetry.

13. The method of claim 12 wherein said heparin is present in the indicator system in a concentration of at least about 750,000 USP Units/L.

14. The method of claim 13 wherein said indicator system includes a standard buffer having a buffering capacity in the pH range of about 7.0 to about 8.5.

15. The method of claim 14 wherein said standard buffer is selected from the group consisting of phosphate, glycine borate, TRIS, MOPS, TES, HEPES, DIPSO, TAPSO, POPSO, HEPPSO, TRICINE, BICINE, TAPS, and mixtures thereof.

16. The method of claim 15 wherein said indicator system is heat aggregated IgG antibody.

17. The method of claim 16 wherein said heparin is present in the indicator system in a concentration of about 1,000,000 USP Units/L.

18. The method of claim 17 wherein said standard buffer is a phosphate buffer.

19. The method of claim 18 wherein said indicator system includes an amount of an hydrophilic nonionic polymer effective to promote agglomeration.

20. The method of claim 19 wherein said hydrophilic nonionic polymer is polyethylene glycol and is present in the indicator system in a concentration of at least about 7.5 g/L.

* * * * *